(12) United States Patent
van Ooijen et al.

(10) Patent No.: US 11,169,161 B2
(45) Date of Patent: Nov. 9, 2021

(54) DEVICE, SYSTEM AND METHOD FOR DETERMINING A FIBRINOGEN LEVEL IN A BLOOD SAMPLE (71) Applicant: KONINKLIJKE PHILIPS N.V., Eindhoven (NL)

(72) Inventors: Hendrik Jan van Ooijen, Eindhoven (NL); Bart Jacob Bakker, Eindhoven (NL); René van den Ham, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 667 days.

(21) Appl. No.: 15/535,784

(22) PCT Filed: Dec. 17, 2015

(86) PCT No.: PCT/EP2015/080379
§ 371 (c)(1),
(2) Date: Jun. 14, 2017

(87) PCT Pub. No.: WO2016/097234
PCT Pub. Date: Jun. 23, 2016

(65) Prior Publication Data
US 2017/0350906 A1     Dec. 7, 2017

(30) Foreign Application Priority Data

Dec. 18, 2014 (EP) .................................... 14198867

(51) Int. Cl.
*G01N 33/86* (2006.01)
(52) U.S. Cl.
CPC ......... *G01N 33/86* (2013.01); *G01N 2333/75* (2013.01)

(58) Field of Classification Search
None
See application file for complete search history.

(56) References Cited

U.S. PATENT DOCUMENTS 5,137,832 A    8/1992  Levine et al.
6,524,861 B1   2/2003  Anderson
(Continued)

FOREIGN PATENT DOCUMENTS

CN    101561441 A    10/2009
EP      2546637 A1    1/2013
(Continued)

OTHER PUBLICATIONS

Cheng Feng, et al., "A comparison of Five Methods for Measuring Fibrinogen", Clinic Examination Magazine, the first volume, the first issue, 2000.
(Continued)

*Primary Examiner* — Lore R Jarrett (57) ABSTRACT

The present invention relates to device (10) for determining a fibrinogen level (20) in a sample (22) comprising, a first input for obtaining an attenuance signal (24) over time indicative of a fibrin polymerization of said sample (22), a second input for obtaining a reactant concentration signal (28) over time indicative of a reactant concentration in said sample (22), wherein the reactant is any substance leading to the cleavage of fibrinogen to fibrin, a simulation unit (16) running a model (32) using the reactant concentration signal (28) as an input to provide a simulated attenuance signal (34) over time, and an evaluation unit (18) configured to infer the fibrinogen level (20) of said sample (22) by comparing the attenuance signal (24) over time with the simulated attenuance signal (34) over time.

15 Claims, 5 Drawing Sheets

(56) References Cited

U.S. PATENT DOCUMENTS

| | | |
|---|---|---|
| 7,074,582 B2 | 7/2006 | Fischer et al. |
| 2002/0019706 A1 | 2/2002 | Braun et al. |
| 2004/0219680 A1 | 11/2004 | Carroll et al. |
| 2011/0014640 A1 * | 1/2011 | Yamamoto ......... G01N 21/5907 435/13 |
| 2014/0118356 A1 | 5/2014 | van Ooijen et al. |
| 2014/0128707 A1 | 5/2014 | Bakker et al. |

FOREIGN PATENT DOCUMENTS

| | | | | |
|---|---|---|---|---|
| GB | 0059277 A1 * | 9/1982 | ............. | G01N 21/82 |
| WO | WO2012172497 | * 12/2012 | ............. | G06F 19/00 |

OTHER PUBLICATIONS

Rio Kita et al., "Formation of Fibrin Gel in Fibrinogen-Thrombin System Static and Dynamic Light Scattering Study", Biomacromolecues, 2002.

Zhou, Weiping, "A comparison of Two Methods for Measuring Fibrinogen", Thrombus and Haemostaseology, the first volume, the first issue, 2014.

Karsaj, et al., "A mathematical model of evolving mechanical properties of intraluminal thrombus", Biorheology, Jan. 2009, 46(6), pp. 1-22.

Sato, et al., "Kinetic Study on The Initial Stages of the Fibrinogen-Fibrin Conversion of Thrombin", Thrombosis Research, Tarrytown, NY, vol. 33, No. 6, Mar. 15, 1984, pp. 645-651.

Weisel, et al., "Computer modeling of fibrin polymerization kinetic correlated with electron microscope and turbidity observations: clot structure and assembly are kinetically controlled", Biophysical Journal, vol. 63, No. 1; Jul. 1, 1992, pp. 111-128.

* cited by examiner

DEVICE, SYSTEM AND METHOD FOR DETERMINING A FIBRINOGEN LEVEL IN A BLOOD SAMPLE

CROSS-REFERENCE TO PRIOR APPLICATIONS

This application is the U.S. National Phase application under 35 U.S.C. § 371 of International Application No. PCT/EP2015/080379, filed on Dec. 17, 2015, which claims the benefit of European Application No. 14198867.5, filed Dec. 18, 2014. These applications are hereby incorporated by reference herein, for all purposes.

FIELD OF THE INVENTION

The present invention relates to a device, system and method for determining a fibrinogen level in a blood sample using a model of fibrin polymerization that is able to simulate the turbidity build-up during a coagulation process based on a time-variant input of a reactant concentration. The model is independent of calibration plasma and standard curves.

BACKGROUND OF THE INVENTION

Hemostasis is the ability of the body to stop blood loss from a vascular injury; the main process involved in hemostasis is the formation of a hemostatic plug in response to the injury often referred to as primary and secondary hemostasis. In healthy situations the hemostatic plug covers the wound in the vasculature quickly and precisely and thereby stops the blood leakage from the wound without interrupting the blood flow in the vessel too much. In pathological situations this hemostatic balance can be disturbed resulting in on the one hand too much clotting or on the other hand excessive bleeding. Examples of thrombosis are venous thrombosis/thromboembolism, pulmonary embolism, ischemic stroke and examples of bleeding are intracranial hemorrhage, hemophilia. The hemostatic imbalance can be a result of three causes, hyper/hypocoagulability, hemodynamic changes or endothelial injury or dysfunction, historically also known as Virchow's triad.

Fibrinogen is an important protein involved in coagulation. During normal blood flow, fibrinogen is soluble; however upon activation of the coagulation system fibrinogen is eventually converted by thrombin into fibrin. Fibrin subsequently polymerizes into insoluble fibrin fibers that, together with (activated) platelets, form a clot. The normal level of fibrinogen is approximately 2.5 g/L (range about 1.5-3 g/L). Yet in many cases the fibrinogen level might be outside the normal range, which might be associated with pathological disorders. For example, in hereditary hypofibrinogenemia patients with exceptionably low levels of fibrinogen result in a bleeding tendency. Also trauma or surgery patients might develop a low level of fibrinogen due to sustained bleeding, resulting in a dangerous situation which can be countered by the addition of blood products. On the other side of the spectrum elevated levels of fibrinogen are found to be correlated with an elevated risk of myocardial infarction, thrombosis and prolonged inflammatory processes such as rheumatoid arthritis.

As a result of these varying fibrinogen levels and associated pathologies, the fibrinogen level test is a valuable clinical test. Many methods have been developed to accurately detect the level of fibrinogen in a plasma or blood sample, see for example Palarati et al. for an overview of available techniques. Unfortunately, all present methods are either very labor-intensive, such as the clot-recovery method, or need a standard curve derived from a plasma sample with a known fibrinogen level to infer the sample's fibrinogen level, such as the Clauss assay or prothrombin-time-derived method. Whereas the former involves a lot of hands on time and therefore is difficult to automate, the latter needs calibration plasmas to be included in the test kit, thereby making these methods less suitable to incorporate in e.g. a handheld point of care (POC) system to detect the level of fibrinogen.

Since reliable point of care fibrinogen tests are not available and central lab test ordering in general takes too long for time-critical situations, there is a need for an improved system and method.

SUMMARY OF THE INVENTION

It is an object of the present invention to provide a device for determining the fibrinogen level in a sample that is more reliable, easy to use and independent from external references. Furthermore, a corresponding system and method shall be provided.

According to a first aspect of the present invention a device for determining a fibrinogen level in a sample is presented comprising, a first input for obtaining an attenuance signal over time indicative of a fibrin polymerization of said sample, a second input for obtaining a reactant concentration signal over time indicative of a reactant concentration in said sample, wherein the reactant is any substance leading to the cleavage of fibrinogen to fibrin, a simulation unit running a model using the reactant concentration signal as an input to provide a simulated attenuance signal over time, and an evaluation unit configured to infer the fibrinogen level of said sample by comparing the attenuance signal over time with the simulated attenuance signal over time.

According to a second aspect of the present invention a system for determining a fibrinogen level in a sample is presented comprising, a measuring unit for providing an attenuance signal over time indicative of a fibrin polymerization of said sample, and a device comprising, a first input for obtaining an attenuance signal over time indicative of a fibrin polymerization of said sample, a second input for obtaining a reactant concentration signal over time indicative of a reactant concentration in said sample, wherein the reactant is any substance leading to the cleavage of fibrinogen to fibrin, a simulation unit running a model using the reactant concentration signal as an input to provide a simulated attenuance signal over time, and an evaluation unit configured to infer the fibrinogen level of said sample by comparing the attenuance signal over time with the simulated attenuance signal over time.

According to a third aspect of the present invention a method for determining the fibrinogen level in a sample is presented comprising, obtaining an attenuance signal over time indicative of a fibrin polymerization of said sample, obtaining a reactant concentration signal over time indicative of a reactant concentration in said sample, wherein the reactant is any substance leading to the cleavage of fibrinogen to fibrin, running a model using the reactant concentration signal as an input to provide a simulated attenuance signal over time, and inferring the fibrinogen level of the sample by comparing the attenuance signal over time with the simulated attenuance signal over time.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

The present invention is based on the general idea of simulating the coagulation process, in particular the turbidity build-up over time, of plasma or a blood sample using a model representative of the underlying biochemical reactions, and by comparing the results thereof with actual measurements taken from the sample after the coagulation process has been initiated by adding a reagent to the sample. The model, for instance a computational model, is designed to simulate aspects of the coagulation process using time variant concentration levels of one or more reactant of the reagent as its input. Herein a reactant is any substance leading to the cleavage of fibrinogen to fibrin, resulting in the polymerization of fibrin monomer. Preferable, the reactant is thrombin.

Subsequently, the fibrinogen level of the sample may be derived from the comparison of the simulated data and the actual measurements using analytical methods.

Advantageously, the present invention requires no additional references. In particular, the present invention requires no standard curves or reference plasma to derive the fibrinogen level of the sample. Therefore, the invention may be used in a standalone, and preferably mobile, point of care system, such that an off-site and time consuming central lab test becomes obsolete. Hence, the present invention may advantageously be used in time-critical situations, e.g. in the operating environment or emergency department.

Finally, the present invention offers more precise results than equivalent tests, since the results are built around the actual underlying biochemical reactions of the coagulation process. In other words, the model is based on analytical data rather than empirical derived data of the coagulation process. Additionally, the model may be further enhanced and optimized if more aspects of the coagulation process should emerge in the future.

Preferred embodiments of the invention are defined in the dependent claims. It shall be understood that the claimed methods, processor, computer program and medium have similar and/or identical preferred embodiments as the claimed system and as defined in the dependent claims.

According to an embodiment, the simulation unit is configured to provide to the evaluation unit multiple simulated attenuance signals over time for a range of fibrinogen levels. In this case the fibrinogen level of the sample is inferred from the plurality of simulated attenuance signals. For that, preferably, a characteristic feature of these signals is extracted and interpolated as a function of fibrinogen levels, such that an equivalent feature extracted from the measured attenuance signal may be mapped against said function to determine the fibrinogen level of the sample. Advantageously, the simulation runs only once to produce the necessary output from the model and can run in parallel with the measurement. Furthermore, the simulated data may be used for multiple subsequent measurements.

According to a further embodiment, the evaluation unit is configured to extract one or more characteristic features from the attenuance signal and further one or more characteristic features from the simulated attenuance signal, wherein the evaluation unit is further configured to match the one or more characteristic features with the further one or more characteristic features. Extracting only specific features of the signal facilitates an easier matching of the simulated and measured signals and thus produces more reliable results, since certain deficiency in the measurement or the simulation may be canceled out. Furthermore, the computation complexity may be reduced using this approach, since only parts of the signals have to be compared with one another, instead of the whole signal.

Preferably, at least one of the one or more characteristic features and at least one of the further one or more characteristic features is defined by the difference between an initial attenuance and a final, that is after the clotting process is (near) fully developed, attenuance of the attenuance signal and the simulated attenuance signal. Since the attenuance signals generally have a sigmoid-like shape with an initial plateau at the beginning and a final plateau at the end, the initial and final attenuance represent an easy to extract, yet highly distinguishing feature of said attenuance signals.

According to a further embodiment, the simulation unit is configured to rerun the model at least one more time with a parameter provided by the evaluation unit, such that an error between the attenuance signal and the simulated attenuance signal is minimized. Such iterative approach may make use of well-known algorithm such as the simplex algorithm, (quasi-)Newton method, gradient descent, genetic algorithm, or differential evolution, and may as such use standard and optimized libraries and modules available in common simulation tools. This way a simple and highly efficient implementation of the model is feasible.

According to a further embodiment, the simulation unit is configured to run the model that uses at least one ordinary differential equation indicative of a chemical reaction of fibrin polymerization. Ordinary differential equations (ODEs) have proven to be very well suited to model the reactions rates of the underlying chemical reactions. Chemical reactions in the form of $A+B \leftrightarrow C$ can straightforwardly be converted into computer-interpretable (algebraic) equations by constructing ODEs or sets of ODEs. Enzymatic and complex assembly processes taken place in the fibrin polymerization can be represented by a set of chemical reactions of the above mentioned form.

Preferably, a state variable of said at least one ordinary differential equation is the reactant concentration signal. Having a time-variant input, such as the reactant concentration over time in the sample, produces very accurate and reliable results, since the underlying chemicals reactions are better and more realistically reflected by such input.

According to a further embodiment, the simulation unit is configured to run the model that uses a set of coupled ordinary differential equations, each being indicative of a chemical reaction of fibrin polymerization, and said set is being solved by the simulation unit numerically. Sets of ODEs may advantageously be solved numerically using standard ODE-solvers available in common simulation tools. This way, an easy and robust implementation of the model using common simulation tools is feasible.

According to a further embodiment, the simulation unit is configured to run the model that uses at least a first algorithm to determine concentrations of protein complexes, a second algorithm to determine the average mass/length ratio of fibrin molecules from said concentrations, and a third algorithm to determine the attenuance of the sample from said mass/length ratio. Such a model connects straightforwardly the input signal, namely a reactant concentration signal, with the output, namely a simulated signal of the attenuance.

According to a further embodiment, the reactant concentration signal over time is interpolated from a time-discrete signal to a continuous signal using a reactant specific interpolation formula. If the reactant concentration is determined by measurement, the measured signal will generally be a time-discrete signal, oftentimes showing a high variation. Advantageously, by interpolating such signal using a proven interpolation function a more suitable input for the model may be derived that better reflects the actual concentration levels in the sample.

According to a further embodiment, the reactant concentration is a thrombin concentration. Thrombin is a preferred clotting trigger as it directly converts soluble fibrinogen in the sample into insoluble strands of fibrin and additionally catalyzes many other coagulation-related reactions. Furthermore, a thrombin concentration in a sample can be determined by measurement.

According to a further embodiment, the system comprises a further measuring unit to provide an actual measurement of a reactant concentration of the sample. By measuring the actual reactant concentration of the sample a more realistic input for the model may be provided, such that more accurate simulations may be performed.

Preferably, said further measurement unit is configured to monitor the cleaving of a fluorogenic substrate and to compare it to a constant known reactant activity in a parallel, non-clotting sample. Such a measurement, especially for the determination of a thrombin concentration, provides very precise results and leads to a more accurate simulation.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
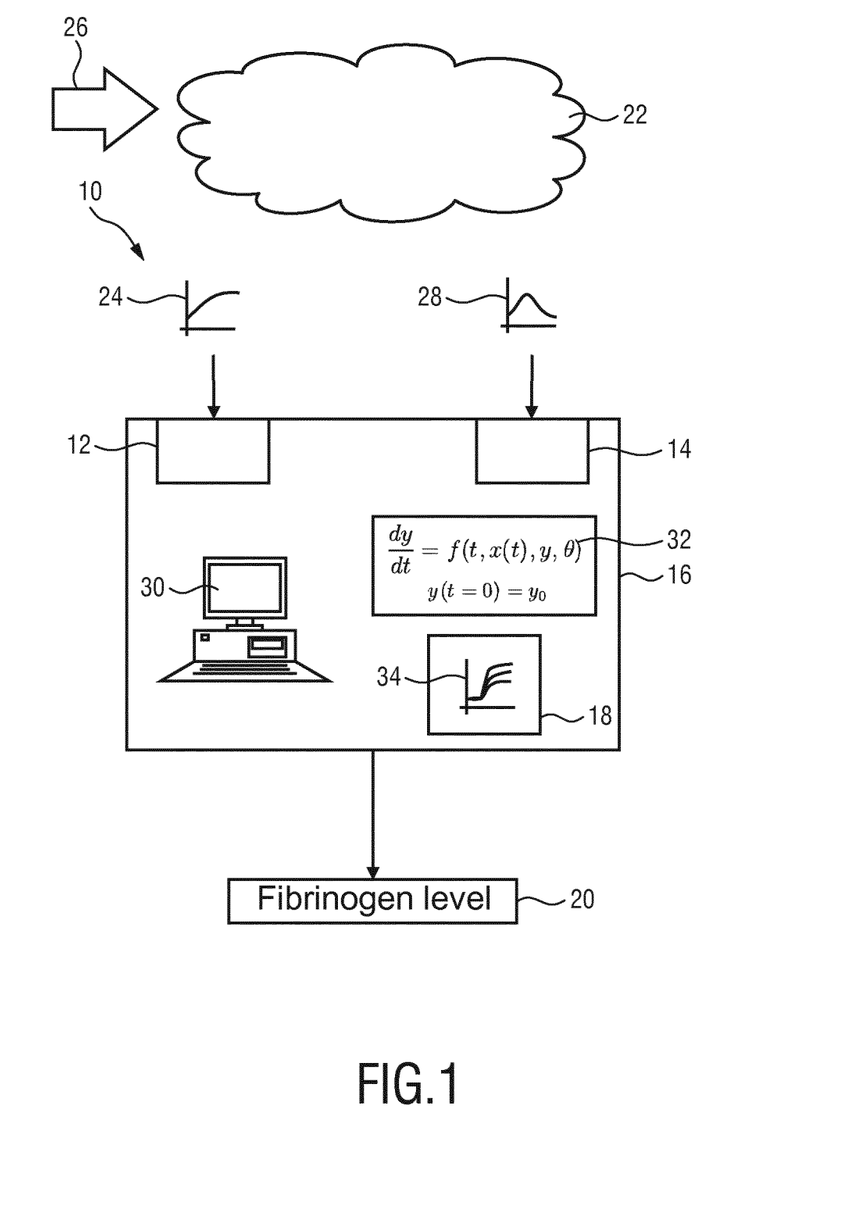
FIG. 1 shows a schematic diagram of an embodiment of a device according to the first aspect of the present invention.

FIG. 1 shows a first embodiment of the device according to the present invention. The device is denoted in its entirety with reference numeral 10. The device comprises a first input 12, a second input 14, a simulation unit 16 and an evaluation unit 18 to determine the fibrinogen level 20 of a sample 22.

The sample 22 is preferably a blood plasma sample, alternatively it can be a whole-blood sample, obtained preferably by venipuncture or alternatively a sample of capillary blood obtained using for example a blood lancet in combination with capillary forces.

The first input 12 can be configured to obtain an attenuance signal 24 indicative of a polymerization of the sample 22 after a clotting trigger 26 has been applied thereto. The attenuance signal 24 is representative of the formation of a fibrin network taking place during blood coagulation. In short, proteins in human plasma, called coagulation factors, respond in a complex cascade as result of a clotting trigger resulting ultimately in the formation of fibrin monomers that polymerize to form fibrin strands. These fibrin strands are highly connected and as a result have a gel-like structure.

The attenuance of a coagulating plasma or blood sample changes over time as a result of the fibrin network being formed during clotting of the sample. Fibrin fibers are being formed after a clotting trigger is added to the sample. These fibrin fibers result in scattering of the incident light resulting in less photons arriving at the detector. Actual absorbance of the photons and other causes of photon loss e.g. due to interference are considered to be constant over time during clotting, hence the attenuance and thereby decrease in transmittance and increase in optical density, which is the base-10 logarithm of the transmittance, is considered solely due to scattering of the incident light by the fibrin fibers formed in the sample. The attenuance of a material is $\log 10(P_0/P)$, where $P_0$ is the radiant power incident on a sample, and P is that transmitted by it. This quantity is also $-\log 10(T)$, where T is the transmittance. Attenuance is often referred to in the literature by terms such as 'optical density', 'turbidity' or 'extinction'. Also the name 'absorbance' (symbol: A) is often used for this quantity, but this is clearly inappropriate for the quantity when the attenuation of the radiation is due to scattering rather than absorption. The quantity itself is called attenuance (symbol: D), with the remark that attenuance reduces to absorbance when there is negligible scattering or reflection. It shall be noted that in the case that attenuance reduces to scattering, scientist may use the term 'turbidity', which is typically considered as $-\ln(T)$. In the latter case, 'turbidity' may be estimated by measuring transmittance. To actually measure scattering due to particles in solution, specialized techniques are available such as small-angle scattering or nephelometry. A person skilled in the art is able to convert what is claimed herein to the turbidity, transmittance, optical density, absorbance and possible other measures of light attenuation, or more preferable scattering due to particles in solution, in a sample.

The attenuance signal 24 may be an analogous or digital signal indicative of a intensity attenuation of transmitted light due to scattering or absorption of light in the sample 22, from which a turbidity or a absorbance property of the sample may be derived.

The second input 14 can be configured to obtain a reactant concentration signal 28 indicative of a reactant concentration in the sample 22. The reactant concentration signal 28 may be an analogous or digital signal representing a concentration of a reagent added to the sample as clotting trigger 26 or any other concentration of intermediate reactants involved in the coagulation process. It shall be noted that the second input 14 is not limited to obtain a single signal, but may also receive further signals indicative of reagent concentrations involved in the coagulation process or other process variables. The second input 14 may obtain the reactant concentration signal 28 directly from the amount of clotting trigger 26 added to the sample 22, for instance, as a manual input, or by an actual measurement taken from the sample 22 after a clotting trigger 26 has been added, wherein the latter is preferred.

Figure 2:
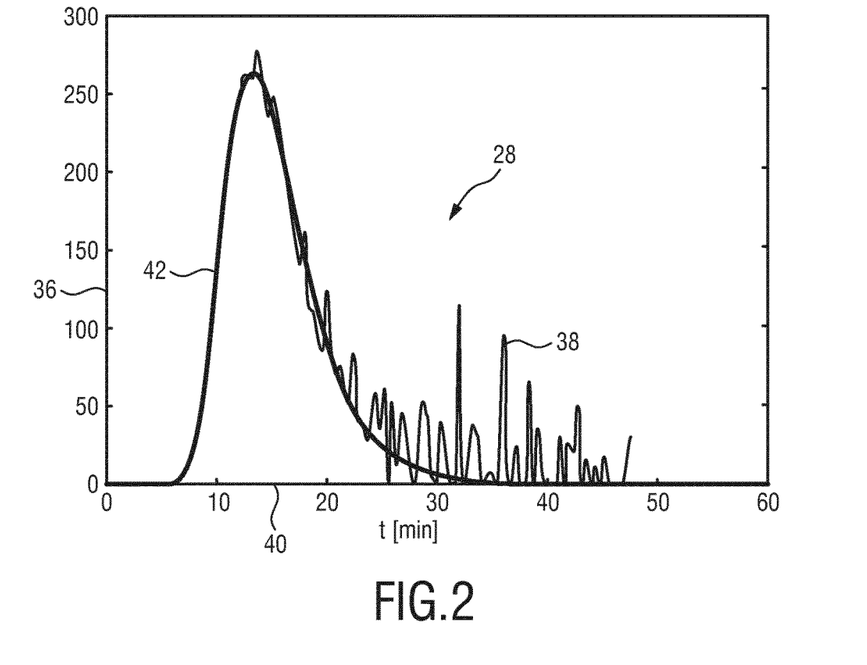
FIG. 2 shows an example of a measured time-discrete signal, showing a high variation reactant concentration signal over time (thin line) and interpolated reactant concentration signal over time (thick line) that serves as input for the model.

In a preferred embodiment the reactant concentration signal 28 may be indicative of a concentration of thrombin available as clotting trigger 26 to the sample 22 as described in more detail with regard to FIG. 2. It shall be noted that the coagulation does not need to be started with the addition of thrombin. Other tissue factor may be added instead and the concentration of thrombin is measured over time to derive the reactant concentration signal 28. In a preferred embodiment the thrombin concentration added is greater than 1 NIH U/mL.

Alternatively, in another embodiment, a snake venom thrombin-like enzyme (SVTLE) such as batroxobin or reptilase may be used to trigger the coagulation, wherein, advantageously, the SVTLE is not inhibited by natural inhibitors in the plasma sample.

The reactant concentration signal 28 and the attenuance signal 24 represent the input to the simulation unit 16 and the evaluation unit 18 which in combination are capable of determining the fibrinogen level 20 in the sample 22. In a preferred embodiment, the simulation unit 16 and the evaluation unit 18 are combined in a single computing device as illustrated here by the computer 30. The computing device may be a standalone PC, a workstation, one or more module in a Clinical Decision Support (CDS) system, a dedicated computing device, or distributed computing means provided, for instance, as a web service.

The simulation unit 16 is configured to execute and run a model 32 using one or more reactant concentration signal 28 as input. Preferably, the model is a computational model. An output of the simulation unit 16 may inter alia include one or more simulated attenuance signals for a range of different fibrinogen levels as denoted here with reference numeral 34.

The evaluation unit 18 is configured to infer the actual fibrinogen level 20 of the sample 22 from the measured attenuance signal 24 and the one or more simulated attenuance signal 34 provided by the simulation unit 16.

In the following, the model 32 run by the simulation unit 16 and inferring of the actual fibrinogen level 20 by the evaluation unit 18 is explained in greater detail with reference to FIGS. 2 and 3 and FIGS. 4 and 5, respectively.

The model 32 may be a mathematical representation of fibrin polymerization, wherein the polymerization of fibrin is a combination of enzymatic and polymerization reactions which can be described as chemical reactions in the form of $A+B \leftrightarrow C$.

The model 32 incorporates these chemical reactions as computer-interpretable (algebraic) equations in order to simulate the fibrin polymerization. Preferably, the chemical reactions are represented hereto, as a set of coupled ordinary differential equations (ODEs) describing the reaction rates of the chemical reactions. In general form an ODE is given by:

$$\frac{dy}{dt} = f(t, y, \theta)$$
$$y(t = 0) = y_0$$

With $\theta$ being an m-dimensional vector containing all reaction rate parameters, y being an n-dimensional vector of the states (here concentrations of the different enzymes and polymerization elements included in the model), t being time, and $y_0$ being a vector of numerical values for y at t=0. Function f is a given vector function, which is a representation of the reactions incorporated in the model.

Examples of individual reactions incorporated in the model may be the following:

representing the cleavage of fibrinopeptide A from the inactivated fibrinogen monomer. First F2a binds to the A-site and subsequently F2a and fibrinogen can either dissociate or F2a can cleave the fibrinogen monomer:

as r1, but now fibrinopeptide B is cleaved:

as r2, but now fibrinopeptide B is cleaved from the partially activated desAA fibrin monomer, which can be part of a protofibril:

as r1, but now fibrinopeptide A is cleaved from the partially activated fibrin monomer:

another F2a binds to the unoccupied B-site of the Fn-F2a(A) complex. This complex can either dissociate or F2a can cleave off FpA from the complex:

as r5, but here F2a binds to the unoccupied A-site and FpA is cleaved off:

Protofibril formation/growth $\forall n, m=1, \ldots, 29$ with $P_1$ being desAA Fn or Fn:

Fiber initiation, F1 are protofibrils of a certain length with $F_1=P_n$ with $P_n$ $\forall n=1, \ldots, 30$:

Fiber growth $\forall k=1, \ldots, 11, l=1, \ldots, 10$:

Such chemical reactions may be converted into reaction rate equations representing the rate of change of concentrations of the involved molecules. For a reversible conversion of molecule A and B into molecule C the reaction rate v may be given as $v=k_+[A][B]-k_-[C]$ with the brackets denoting concentrations. The associated ODEs can be expressed as:

$$\frac{d[A]}{dt} = -v$$
$$\frac{d[B]}{dt} = -v$$
$$\frac{d[C]}{dt} = +v$$

For irreversible reactions the term $k_-[C]$ may be set to zero. The ODE of a particular molecule is the summation of all reaction rates the molecule is involved in.

In a preferred embodiment the model may result in 144 ODEs/states of which 12 belong to the enzymatic part and 132 to the protofibril and fiber formation. Such a set of coupled ODEs may be solved numerically using standard ODE-solver available, for instance, in MATLAB (The MathWorks Inc., Natick, Mass., USA) or other numerical computation tools.

From the molecule concentrations obtained by the ODEs over time a simulated attenuance of the sample may be derived. In a sample of polymerizing fibrin most of the attenuation of light is a result of light scattering on the surface of the formed fibers. Therefore, the attenuation of the light intensity may be defined as the integral over all scattering angles. The scattering due to thin rod-like particles, like fibers, can be estimated using the Rayleigh scattering theory which describes the elastic scattering of light or other electromagnetic radiation by particles much smaller than the wavelength of the light.

To be able to connect the simulated time-profiles of the concentrations of protein (complexes) obtained from the ODEs to the attenuance, the mass/length of the simulated fibrin molecules may be determined. The average mass/length ratio of the simulated fibrin molecules (in whatever configuration, e.g. monomers, protofibrils, fibers) is the mass/length ratio of each particle weighted by their concentration:

$$\mu_{mdl} = \sum_{i=1}^{n} \frac{c_i}{c_{total}} \mu_i$$

With $c_i$ being the concentration of a particle i, $c_{total}$ being the concentration of all particles, and $\mu_i$ being the mass/length ratio of particle i calculated by using the number of monomers and position of the monomers in the particle (e.g. monomer, protofibril, fiber, etc.) in combination with the weight and length of a single monomer. For every particle the average number of monomers in the longitudinal and lateral direction may be monitored during the simulation, thereby making it possible to calculate the mass/length ratio at every time point. Furthermore, the length of a particle containing more than one fibrin monomers may be approximated using:

$$L_p = \tfrac{1}{2}(N_{longitudinal}+1)L_{monomer}$$

With $N_{longitudinal}$ being the (average) number of monomers in the longitudinal direction of the fiber and $L_{monomer}$ being the length of a single monomer, i.e. 45 nm. The factor ½ is the result of the half-staggered formation of fibers. Obviously, fibrinogen and fibrin monomers are assigned a length of 45 nm.

The average radius r of the particles needed in order to calculate the attenuance may be derived by estimating the average radius of the particles in the solution using the known density of a fibrin network, which is approximately 0.28 g/cm³, in combination with the assumption that the shape of fibers are by approximation equal to a cylindrical volume.

Finally, taking the above estimations into account, the simulated attenuance may be calculated using:

$$\tau = \frac{c}{\lambda^3 \left( \frac{A}{\mu} + \frac{B}{\pi \rho N_A \lambda^2} \right)}$$

With $N_A$ being Avogadro's number to transform the density to Da/cm³, $\mu$ being the average mass/length ratio of the fibers in Dalton per centimeter, and A and B being lumped parameters that can be determined in separate experiments or by measuring the attenuance of a fixed mass/length ratio of known solute concentrations at different wave lengths. In a preferred embodiment values for A and B at a wavelength of 632.8 nm may be $6.76 \times 10^{22}$ and $1.41 \times 10^{24}$, respectively.

FIG. 2 depicts in a diagram an example of a reactant concentration signal 28 which may be used as input to the model 32 of the simulation unit 16. Here, the reactant concentration signal 28 represents a thrombin concentration 36 (axis of ordinate) in the sample 22. Thrombin may be used as preferred clotting trigger 26. It acts as a serine protease that converts soluble fibrinogen in the sample 22 into insoluble strands of fibrin and catalyzes many other coagulation-related reactions. The fibrin strands subsequently polymerize by forming a fibrin network, causing a gelation of the plasma that can be measured inter alia by determining the attenuance as explained above. It shall be noted that the system is not limited to thrombin as reagent as illustrated here; other protein with similar activity towards fibrinogen or even a combination of different reagents are conceivable as well.

The thrombin concentration 36 depicted in FIG. 2 results from an actual measurement 38 of the thrombin concentration in the sample over time 40 (axis of abscissas). In another embodiment the thrombin concentration of the sample may be derived by the amount of thrombin added as clotting trigger 26 to the sample 22. Alternatively, the thrombin concentration may be estimated by its initial concentration values and treated as constant value over time. Generally, an actual measurement 38 of the reactant concentration in the sample over time is preferred. Such measurement may be conducted in parallel, in series, or simultaneously to the measurement of the attenuance signal 24.

Furthermore, the actual time-discrete measurement 38 of the thrombin concentration may be approximated by means of interpolation, for instance, using the following interpolation formula (Wagenvoord et al. J Thromb Haem 4: 1331-1338):

$$W = abc \times e^{-bc(t-t_0)} \times (e^{b(t-t_0)} - 1)^{c-1}$$

With t being time, and a, b, c and to being positive constants that have been fitted to the experimentally determined thrombin concentration data.

In a preferred embodiment the interpolation may be further enhanced by a hybrid interpolation of the time discrete attenuance signal 38 using a cross-over fit of an exponential fit combined with the above stated W-function. The hybrid fit will follow the fitted exponential curve until it crosses with the fitted W-function, wherein the transition may be made at a thrombin concentration of 20 nM arbitrarily if the two functions do not intersect. The result of the interpolation is a continuous signal 42, which is subsequently being used as input to the model 32. In other words, the input to the model 32 is preferably an interpolated, continuous signal 42 derived from a time-discrete or continuous measurement 38.

Figure 3:
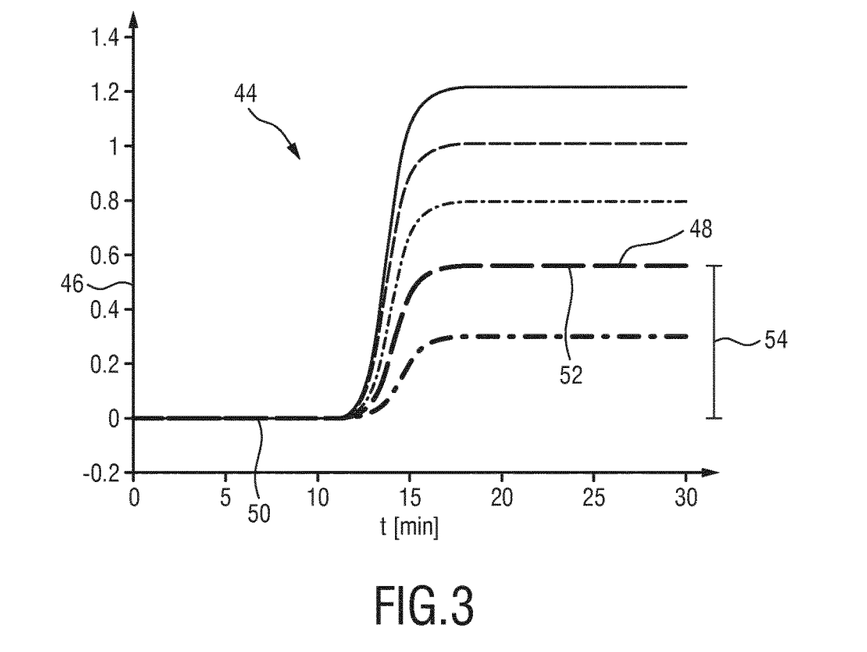
FIG. 3 shows an example of multiple simulated attenuance signals over time for the same reactant concentration signal over time with increasing values of fibrinogen resulting in a stepwise increase in attenuance.

With reference to FIG. 3 an example of an output of the model 32 is described. The diagram shows a plot 44 of multiple simulated attenuance signals 34 over time for a range of different fibrinogen levels. The attenuance 46 is plotted here on the vertical axis and time 40 on the horizontal axis. Reference numeral 48, for instance, denotes a simulated attenuance signal for a fibrinogen level of 2 g/L. The individual simulated attenuance signals represented by the plot 44 are generally characterized by a sigmoid shape having a starting plateau, an end plateau, and a slope in between, wherein the starting plateau defines an initial attenuance 50 and the end plateau a final attenuance 52, respectively. The difference between the initial attenuance 50 and the final attenuance 52 defines a Δattenuance as denoted here with reference numeral 54 for the exemplary attenuance signal 48 for a fibrinogen level of 2 g/L. The Δattenuance 54 represents a preferred feature of the simulated attenuance signals 44, which is easy to extracted and yet very characteristic. The Δattenuance of the simulated attenuance signals 44 and a Δattenuance extracted from the measured attenuance signal 24 may be used for the comparison of the simulated and the measured attenuance to infer the fibrinogen level of the sample as explained in greater detail with reference to FIG. 4 and FIG. 5 in the following From the model output and the measured attenuance signal 24, the evaluation unit 18 may infer the actual fibrinogen level 20 of the sample 22 by comparing the two inputs with one another. This can be done in a number of ways, for example, by comparing a specific extracted feature, such as the Δattenuance 54, from the measured attenuance signal with the same feature extracted from the simulated attenuance signals 34. Preferably, from the feature extracted from the plurality of simulated attenuance signals 44 a function of said feature over fibrinogen levels is derived. Subsequently, Δattenuance extracted of the measured attenuance signal 24 is mapped against said function to determine the fibrinogen level 20.

It shall be noted that such procedure is not limited to Δattenuance as feature. Other features such as the whole curve, maximum slope of the attenuance signal (max rate), lag time, time to maximum slope, time to plateau and time to lower plateau and so forth, may be used similarly to infer the fibrinogen level. It is also conceivable that multiple features may be used in combination to achieve more reliable results. Furthermore, the comparison may also be based on other outputs of the model of fibrin polymerization, for instance, the time evolution of the average mass/length ratio of the fibrin fibers formed during the polymerization process.

Figure 4:
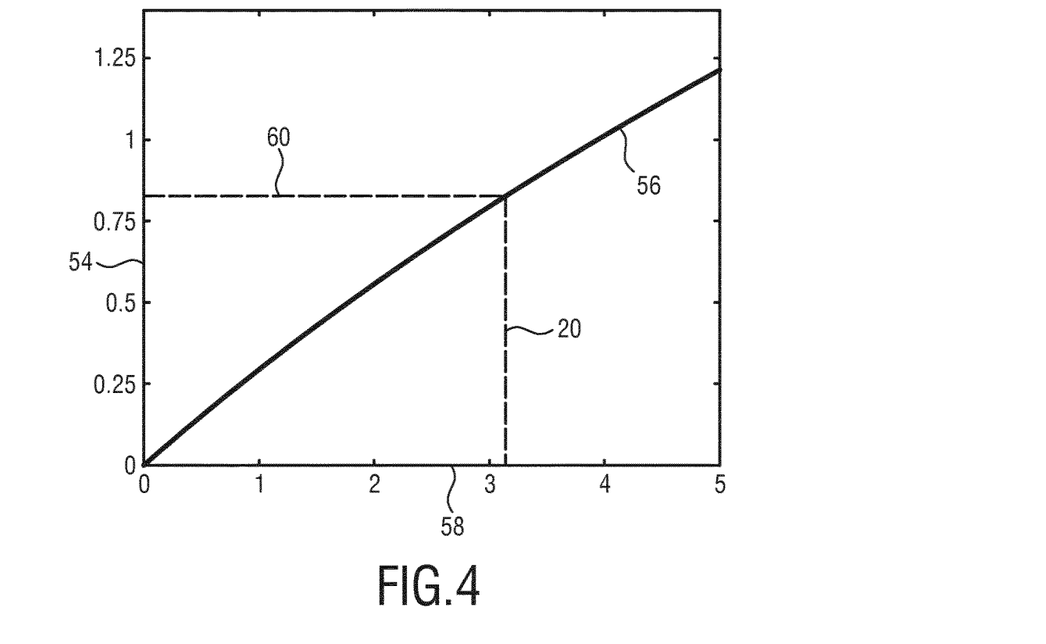
FIG. 4 shows an example of an extracted feature of the simulated attenuance signals as a function of fibrinogen levels.

With reference to FIG. 4 an example of such a comparison using the Δattenuance 54 as the relevant feature is illustrated. FIG. 4 shows a plot 56 of simulated Δattenuance 54 as a function of fibrinogen level 58. From the plot 56 the fibrinogen level 20 of the sample may be derived by mapping the Δattenuance 60 extracted from the measured attenuance signal against this function 56. Here, for example, an actual observed Δattenuance 60 of 0.83 relates to a fibrinogen level 20 of 3.14159 g/L.

Figure 5:
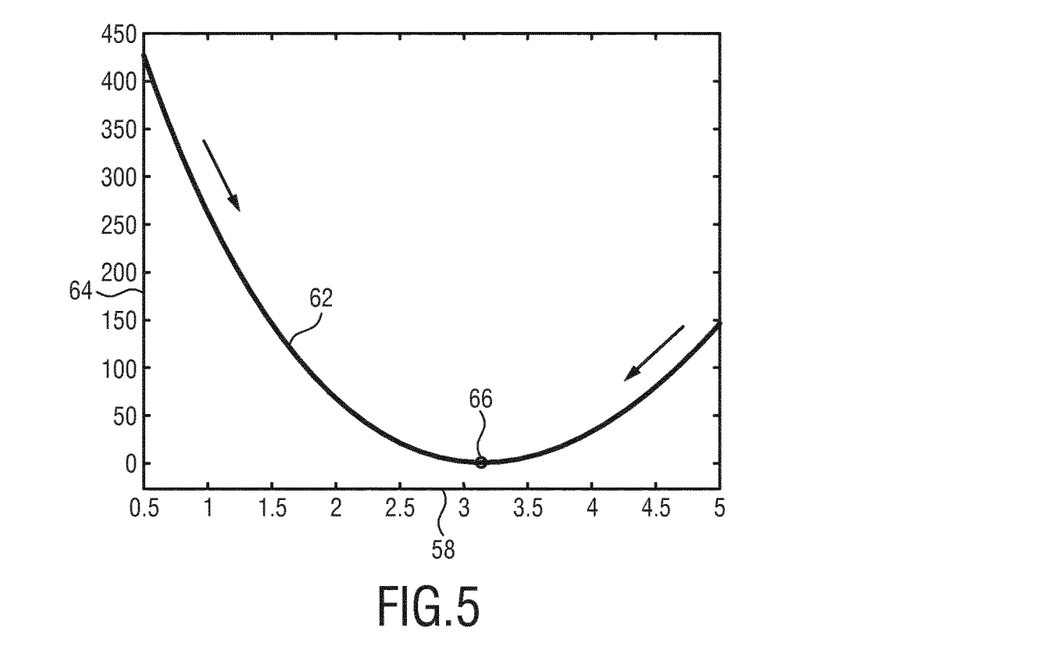
FIG. 5 shows an example of an error signal derived from the comparison of the measured and the simulated attenuance signal as a function of fibrinogen levels.

With reference to FIG. 5 an alternative approach to infer the fibrinogen level from the measured and the simulated attenuance signal is illustrated. Here, the difference between the measured and simulated attenuance signal is minimized by adapting the input parameter for the fibrinogen level of the simulation runs in such a way that the difference between the attenuance signal and the simulated the attenuance signal is minimized. In other word, the evaluation unit reruns the simulation by the simulation unit at least one more time with adapted parameters, in particular different fibrinogen levels, such that a difference between the measured and the simulated attenuance signal, or feature(s) derived thereof, remains under a certain threshold. It shall be noted that the adapted parameters are not limited to different fibrinogen levels. Other parameters are conceivable as well. Known algorithms to be used for such a procedure are, for instance, the simplex algorithm, (quasi-)Newton method, gradient descent, genetic algorithm, and differential evolution.

FIG. 5 illustrates the results of such a procedure, in which an error between the observed attenuance signal and the simulated attenuance signal is being minimized by changing the parameter for the fibrinogen level with each simulation run. The plot 62 of FIG. 5 shows the sum of the squared error 64 as function of fibrinogen level 62, wherein the point reflecting the smallest error, which is here the minimal turning point 66, marks the fibrinogen level of the sample. Here, for instance, a fibrinogen level of 3.14159 g/L is determined as indicated by the open circle. In the given example, the complete signals have been compared. Alternatively, only features of the signal may be used for the comparison instead.

Figure 6:
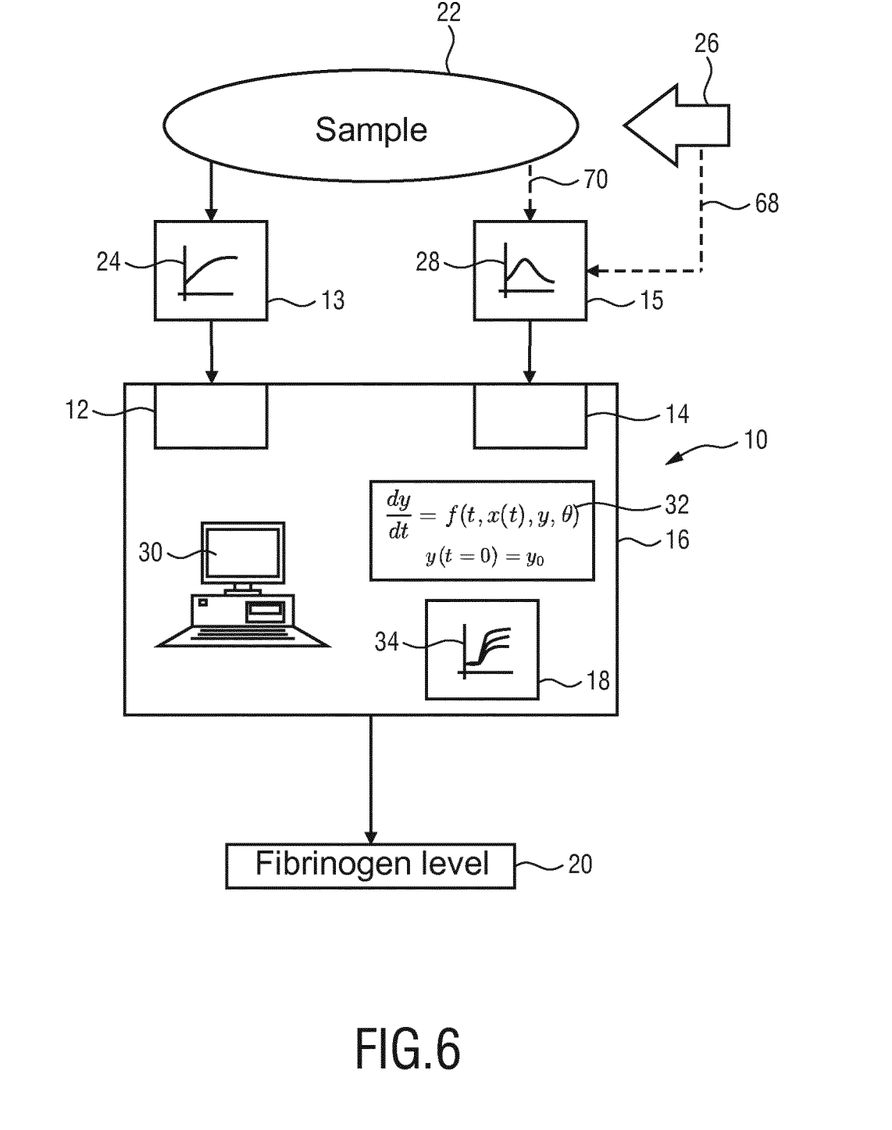
FIG. 6 shows an embodiment of a system according to the second aspect of the present invention.

FIG. 6 shows an exemplary embodiment of a system according to the present invention. The system comprises in this embodiment, a device 10 as explained in detailed with reference to FIG. 1, a measuring unit 13 and a signaling unit 15.

The measuring unit 13 may be any device configured to obtain an attenuance signal 24 indicative of a fibrin polymerization of the sample 22. Preferably, the measuring unit 13 comprises a light source and a corresponding light detector to determine the intensity of light passing through the sample as a function over time. The measurement is preferably provided as an analogous or digital signal and passed on to the first input 12 of the device 10 for processing.

Additionally, the system may comprise a signaling unit 15 which can be any device configured to provide a reactant concentration signal 28 indicative of a reactant concentration in the sample 22. In one embodiment the signaling unit 15 can be a simple input unit for manually providing an initial reactant concentration as a single constant. In a preferred embodiment, the signaling unit 15 comprises a further measuring unit configured to provide an actual continuous measurement indicative of a reactant concentration over time. For that, the further measuring unit may continuously measure the amount of clotting trigger 26 added to the sample 22 as denoted by reference numeral 68, or preferred, the further measuring unit determines the actual reactant concentration from the sample directly. This may be done, for instance, using a calibrated automated thrombin measurement (CAT-TGA) as denoted here with reference numeral 70.

It shall be noted that the signaling unit 15 is not limited to provide a single system. It is conceivable that the signaling unit 15 provides further signals to the input 14 to be used by the simulation unit 16. Furthermore, it shall be noted that the input 12 and the input 14 may only be separate units on a logical level. Input 12 and 14 may as well be combined into a single interface capable of obtaining the relevant signals. Input 12 and input 14 could thus be realized as a single network adapter or as USB port.

From the signal provided by the measuring unit 13 and the signaling unit 15 the device 10 determines the fibrinogen level as explained in detail with reference to FIGS. 1 to 5.

In another embodiment the system may preferably be divided into a testing kit, which comprises cartridges, reagents and so forth to perform the necessary lab experiments to obtain the required input signals, and a device 10, which receives said input signals and performs the simulation and evaluation to determine the fibrinogen level of the sample. The testing kit can be a one-way kit which is disposed after use, whereas the device 10 is preferably reusable.

In another embodiment, the testing kit may be a portable device having two intakes as holding fixtures for the sample and a reagent. A sample may be inserted into the intake and applied with an appropriate reagent inserted into the other intake. Preferably, the reagent will be applied to the sample automatically to avoid any manual error. The portable device may further include measuring units, which take from the sample the necessary measurements to obtain the signals necessary for the simulation and evaluation. The simulation and evaluation is preferably not performed by the portable device itself, but by a computing device link to the portable device. For that, the portable device may be hooked up, preferably wirelessly, to a workstation or a terminal of a clinical decision support system, which may perform the required calculations. The results of said calculations may be return to the portable device and display thereupon, or stored with in the CDS.

Figure 7:
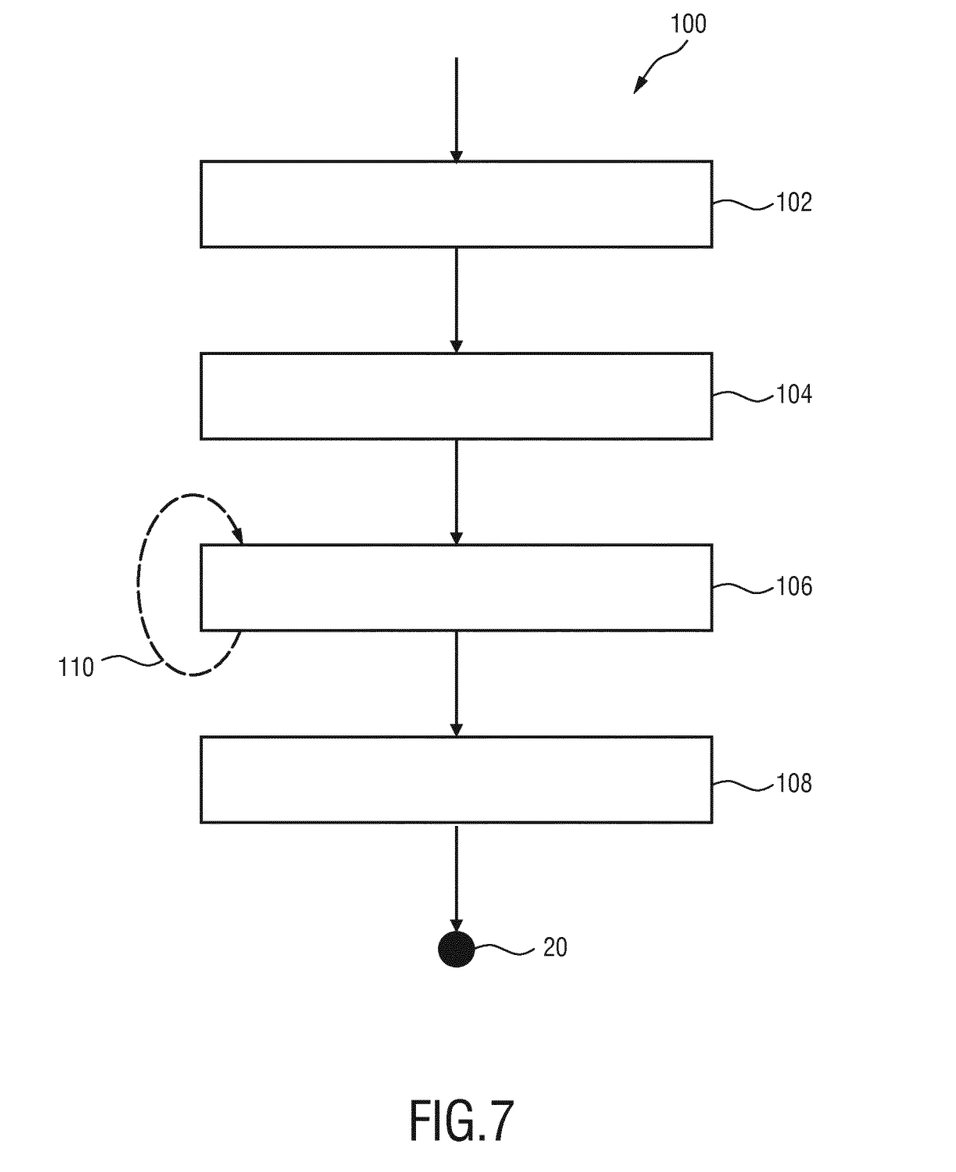
FIG. 7 shows a method according to the third aspect of the present invention.

With reference to FIG. 7 the individual steps of a method 100 according to the present invention are illustrated. The method starts with the input of plasma or a blood sample which is to be analyzed. In a first step 102 an attenuance signal over time is obtained, preferably, from a continuous measurement of the intensity attenuation of light transmitted thought the sample. Such attenuance signal over time may be represented as intensity of light passed through the sample relative to the intensity of a light source that is used to illuminate the sample. Generally, the obtained attenuance signal is a time-discrete signal with time-discrete values. Such signal may be further interpolated to be represented as a continuous signal.

In the following step 104 a further input signal is obtained, namely a reactant concentration signal over time indicative of a reactant concentration in said sample. Such signal may be obtained by a given initial concentration of a reagent or by a direct measurement of the reactant concentration in the sample. The latter may be achieved in case of thrombin being one reactant by a so called Calibrated Automated Thrombin Measurement (CAT-TGA). For that, the cleaving of a fluorogenic substrate will be monitored and compared to a constant known reactant activity in a parallel, non-clotting sample. A standard thrombin generation assay measures every tens of seconds the fluorescence.

Preferably, such measurement is taken from said sample under the same conditions than the measurement of the attenuance signal. Even more preferably, both measurements take place simultaneously with respect to one another. In the alternative, the measurements are conducted in series. The retrieved time-discrete signal may be transferred to a continuous signal as explained in detail with reference to FIG. 2.

Having obtained the attenuance signal over time and the reactant concentration signal over time a model is executed under step 106 with the reactant concentration signal as input. The output of the simulation comprises at least one simulated attenuance signal, which may subsequently be used to infer the fibrinogen level under step 108.

Step 108 can be carried out in multiple ways. The simulated attenuance signal may be a single signal that is iteratively adapted by changing the input parameter for the fibrinogen level to fit the simulated attenuance signal to the previously measured attenuance signal. For that, the simulation may be rerun multiple times as indicated here by the dashed arrow 110 until an error between the simulated and the measured signal, or features thereof, has been minimized. Once the error has been minimized the input parameter for the fibrinogen level represents the fibrinogen level 20 of the sample and the method ends.

Alternatively, there is a plurality of simulated attenuance signals produced by the simulation under step 106. In this case under step 108 a comparison of the measured attenuance signal or features thereof with the simulated attenuance signal is conducted to derive the fibrinogen level 20 of the sample. In a preferred exemplary embodiment the differences of the initial and the final value of the attenuance signals may be determined and interpolated as a function of fibrinogen levels. From said function and the difference of the measured initial and final attenuance the fibrinogen level 20 of the sample may be determined. Other features or the whole signal may be used in the alternative, or additionally to optimize the determination of the fibrinogen level 20. Such other features may be the slope of the signal (max rate), lag time, time to maximum slope, time to plateau, or time to lower plateau.

Additionally, it shall be noted that other outputs of the simulation under step 106 may be used to determine the fibrinogen level 20. One specific alternative may be the time evolution of the average mass/length ratio of the fibrin fibers formed during the polymerization process.

While the individual steps 102 to 108 may be carried out manually, an automated or semi-automated process is preferred. Moreover, method steps or the whole method 100 may be carried out by means of a computer program implemented on a computing device such as a common PC or a workstation. Additionally, the method steps may be executed in different order than depicted in FIG. 7, or may be performed in parallel in respect to one another. It may also be possible to perform some simulation aspects in advance such that in time critical situation only parts of the simulation have to be executed.

Furthermore, simulated data may be stored and reused for subsequent measurements, or to optimize the parameters of the model itself.

Finally, it shall be noted that the method 100 is not limited to the model as disclosed herein, but may be used with other models representative of fibrin polymerization as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a fibrinogen level in a sample comprising:
    a first input for obtaining an attenuance signal over time indicative of a fibrin polymerization of said sample;
    a second input for obtaining a reactant concentration signal over time indicative of a concentration of a reactant in said sample, wherein the reactant is any substance leading to the cleavage of fibrinogen to fibrin;
    a simulation unit running a model using the reactant concentration signal as an input to provide a simulated attenuance signal over time, wherein the model uses an average mass/length ratio of simulated fibrin molecules; and
    an evaluation unit configured to infer the fibrinogen level of said sample by comparing the attenuance signal over time with the simulated attenuance signal over time.

2. The device according to claim 1, wherein the simulation unit is configured to provide, to the evaluation unit, multiple simulated attenuance signals over time for a range of fibrinogen levels.

3. The device according to claim 1, wherein the evaluation unit is configured to extract one or more characteristic features from the attenuance signal and further one or more characteristic features from the simulated attenuance signal, wherein the evaluation unit is further configured to match the one or more characteristic features with the further one or more characteristic features.

4. The device according to claim 3, wherein at least one of the one or more characteristic features and at least one of the further one or more characteristic features is defined by the difference between an initial attenuance and a final attenuance of the attenuance signal.

5. The device according to claim 1, wherein the simulation unit is configured to rerun the model at least one more time with a parameter provided by the evaluation unit, such that an error between the attenuance signal and the simulated attenuance signal is minimized.

6. The device according to claim 1, wherein the simulation unit is configured to run the model which uses at least one ordinary differential equation indicative of a chemical reaction of fibrin polymerization.

7. The device according to claim 6, wherein a state variable of said at least one ordinary differential equation is the reactant concentration signal.

8. The device according to claim 1, wherein the simulation unit is configured to run the model which uses a set of coupled ordinary differential equations, each being indicative of a chemical reaction involved in fibrin polymerization, and said set is being solved by the simulation unit numerically.

9. The device according to claim 1, wherein the simulation unit is configured to run the model which uses at least a first algorithm to determine concentrations of proteins and protein complexes over time, a second algorithm to determine the average mass/length ratio of fibrin molecules from said concentrations, and a third algorithm to determine the attenuance of the sample from said mass/length ratio.

10. The device according to claim 1, wherein the reactant concentration signal over time is interpolated from a time-discrete signal to a continuous signal using a reactant specific interpolation formula.

11. A system for determining a fibrinogen level in a sample comprising:
    a measuring unit for providing an attenuance signal over time indicative of a fibrin polymerization of said sample; and
    the device according to claim 1.

12. The system according to claim 11 further comprising:
    a further measuring unit for providing an actual measurement of a reactant concentration of said sample.

13. The system according to claim 11, wherein the measuring unit and said further measuring unit are configured to produce measurements of said sample in parallel.

14. A method for determining a fibrinogen level in a sample comprising:
    obtaining an attenuance signal over time indicative of a fibrin polymerization of said sample;
    obtaining a reactant concentration signal over time indicative of a concentration of a reactant in said sample, wherein the reactant is any substance leading to the cleavage of fibrinogen to fibrin;
    running a model using the reactant concentration signal as an input to provide a simulated attenuance signal over time, wherein the model uses an average mass/length ratio of simulated fibrin molecules; and
    inferring the fibrinogen level of the sample by comparing the attenuance signal over time with the simulated attenuance signal over time.

15. A non-transitory computer readable medium comprising computer program code stored thereon, the computer readable medium and computer program code being configured to, when run on at least one processor, perform a method for determining a fibrinogen level in a sample, the non-transitory computer readable medium comprising:
   instructions for obtaining an attenuance signal over time indicative of a fibrin polymerization of said sample;
   instructions for obtaining a reactant concentration signal over time indicative of a concentration of a reactant in said sample, wherein the reactant is any substance leading to the cleavage of fibrinogen to fibrin;
   instructions for running a model using the reactant concentration signal as an input to provide a simulated attenuance signal over time, wherein the model uses an average mass/length ratio of simulated fibrin molecules; and
   instructions for inferring the fibrinogen level of the sample by comparing the attenuance signal over time with the simulated attenuance signal over time.

* * * * *